US008247566B2

(12) United States Patent
Savanovic et al.

(10) Patent No.: US 8,247,566 B2
(45) Date of Patent: Aug. 21, 2012

(54) CRYSTALLINE SOLVATE OF OMEPRAZOLE SODIUM

(75) Inventors: Lidija Vranicar Savanovic, Metlika (SI); Zoran Ham, Trbovlje (SI); Janez Rzen, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 727 days.

(21) Appl. No.: 11/916,462

(22) PCT Filed: Jun. 7, 2006

(86) PCT No.: PCT/EP2006/005425
§ 371 (c)(1),
(2), (4) Date: Mar. 10, 2009

(87) PCT Pub. No.: WO2006/131338
PCT Pub. Date: Dec. 14, 2006

(65) Prior Publication Data
US 2009/0221646 A1    Sep. 3, 2009

(30) Foreign Application Priority Data
Jun. 8, 2005   (SI) .................................... 200500172

(51) Int. Cl.
*C07D 401/12*    (2006.01)
(52) U.S. Cl. .................................................... 546/273.7
(58) Field of Classification Search .............. 546/273.7; 514/338
See application file for complete search history.

(56) References Cited

U.S. PATENT DOCUMENTS

| 4,738,974 | A  | 4/1988  | Brandstrom |
| 6,180,652 | B1 | 1/2001  | Tsujii et al. |
| 6,207,188 | B1 | 3/2001  | Gustavsson et al. |
| 6,627,646 | B2* | 9/2003 | Bakale et al. ............... 514/322 |
| 2004/0224987 | A1 | 11/2004 | Reddy et al. |

OTHER PUBLICATIONS

Vippagunta et al., "Crystalline solids", Advanced Drug Delivery Reviews 48 (2001) 3-26.*
Silverman, The Organic Chemistry of Drug Design and Drug Action, NY: Academic Press, Inc. 1993, 72-76.*
Rowland and Tozer. "Clinical Pharmacokinetics, etc.," 1995, p. 123.*
Wilbraham et al. "Organic and biochemistry . . ." p. 250-251 (1985).*
Garattini "Active drug metabolites . . ." Clin. Pharmacokinetics v.10, p. 216-227 (1985).*
CMU Pharmaceutical polymorphism, intenet p. 1-3 (2002) (printout Apr. 3, 2008).*
Singhal et al., "Drug polymorphism, etc., "Advanced drug delivery reviews 56, 335-347 (2004).*
Concise Encyclopedia, NY: Walter de Gruyter Berlin, 1994, 872-873.*
Brittain ed., "Polymorphism in Pharmacetical Science.," NY:Marcel Dekker, Inc., 1999, 1-2, 125-181,183-226, 235-238.*
Jain et al., "Polymorphism in Pharmacy", Indian Drugs, 1986, 23(6) 315-329.*
Ulicky. Comprehensive Dictionary of Physical Chemistry, NY: Prentice Hall, 1992, p. 21.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Caira, "Crystalline Polymorphism, etc.," Topics in Current Chemistry, 198, Springer Verlag Berlin Heidelberg 1998, 163-208.*
Doelker, english translation of S.T.P, Pratiques (1999), 9(5), 399-409, pp. 1033.*

* cited by examiner

*Primary Examiner* — Patricia Morris
(74) *Attorney, Agent, or Firm* — Luedeka Neely Group, P.C.

(57) ABSTRACT

The present invention belongs to the field of pharmaceutical industry and relates to novel crystalline omeprazole sodium ethanol solvate and to the process for its preparation, which acts as intermediate compound to the processes for its conversion into different crystalline forms, first of all to a known omeprazole sodium form A, with low amount of residual solvents, i.e. less than 0.5% by weight of residual solvent.
The present invention also relates to novel crystalline omeprazole sodium form E and crystalline omeprazole sodium form F as well to the processes for their preparation as well, both with considerably low levels of residual solvents.
Omeprazole sodium form A and both novel crystalline forms omeprazole sodium form E and form F are useful for the treatment of gastrointestinal disorders.

4 Claims, 9 Drawing Sheets

CRYSTALLINE SOLVATE OF OMEPRAZOLE SODIUM

This application is the National Stage of International Application No. PCT/EP2006/005425, filed on Jun. 7, 2006, which claims benefit under 35 U.S.C. §119 (e) to Slovenian patent application P200500172 filed on Jun. 8, 2005.

1. Field of the Invention

The present invention belongs to the field of pharmaceutical industry and relates to a novel crystalline ethanol solvate of omeprazole sodium salt. Omeprazole is the generic name of (5)-6-methoxy-2-[[(4-methoxy-3,5-dimethyl-2-pyridinyl) methyl]sulfinyl]-1H-benzimidazole used in the treatment of gastrointestinal disorders. Further, the invention relates to a process for the preparation of crystalline omeprazole sodium ethanol solvate and to the processes for its conversion into different crystalline forms of omeprazole sodium. First of all, the invention relates to a readily feasible and reproducible process of conversion of said novel omeprazole sodium ethanol solvate to an ambient-temperature stable omeprazole sodium of known crystalline form, hereinafter referred to as omeprazole sodium form A, with a low amount of residual solvents.

The present invention relates also to two novel crystalline forms of omeprazole sodium, hereinafter referred to as omeprazole sodium form E and omeprazole sodium form F. Further, the present invention relates to the processes for the preparation of omeprazole sodium form E and omeprazole sodium form F, both with considerably low levels of residual solvents.

Furthermore, the present invention relates to the use of omeprazole sodium form E and omeprazole sodium form F for the treatment of diseases related to gastric acid hypersecretion, and to pharmaceutical compositions containing as active substance omeprazole sodium form E and omeprazole sodium form F.

2. Technical Problem

Chemical stability, solid state stability and "shelf life" of an active pharmaceutical ingredient are important properties for a pharmaceutically active compound. It is generally known that stability of the active pharmaceutical ingredient among others depends also upon residual solvents. Therefore, it is highly desirable to provide a stable and crystalline solid form of the active pharmaceutical ingredient with a low level of residual solvents, preferably in an industrially simple and reproducible process.

There is a constant need for new solid forms of omeprazole sodium and methods of their preparation since it has been observed that a number of drugs exhibit desirable dissolution characteristics and, in some cases, desirable bioavailability patterns when used in a specific solid form. Moreover, properties such as the stability and hygroscopicity of polymorphs may differ.

3. Prior Art

The compound known under chemical name (5)-6-methoxy-2-[[(4-methoxy-3,5-dimethyl-2-pyridinyl)methyl]sulfinyl]-1H-benzimidazole and having the generic name omeprazole is known as a proton pump inhibitor, which inhibits gastric acid secretion. Omeprazole may be used for the treatment of gastric acid related disorders and gastrointestinal inflammatory diseases in mammals and especially in man, including e.g. gastro-esophageal reflux, esophagitis, heartburn, gastritis, hypersecretory conditions (e.g. Zollinger-Ellison, endocrine adenoma), duodenitis, gastric ulcer and duodenal ulcer. Omeprazole is also useful for treating infections such as those caused by *Helicobacter pylori*. Omeprazole and pharmaceutically acceptable salts thereof were first described in patent EP-B-5129.

The specific alkaline salts of omeprazole, such as the sodium salt, were first described in patent EP-B-124 495. Omeprazole sodium salt prepared according to examples 1 and 2 of EP-B-124 495 is unstable and a mixture of crystal forms and amorphous material. One of the crystal forms present in the mixture is omeprazole sodium form A and is a hydrate with one to two molecules, of which one water molecule is strongly bound in the crystal structure while the other is easily removed by drying. The resulting dried substance containing one strongly bound water molecule is very hygroscopic and absorbs water rapidly under normal conditions.

Well-defined omeprazole sodium monohydrate salt, hereinafter referred to as omeprazole sodium form B, and preparation thereof is disclosed in U.S. Pat. No. 6,207,188. According to the description, omeprazole sodium form B is a crystalline form exhibiting advantageous properties, such as being well-defined, thermodynamically stable, non-hygroscopic and being a true monohydrate crystal form. In contrast to form B, the patent describes omeprazole sodium form A as a thermodynamically unstable form which can under certain storing conditions be completely or partly converted to omeprazole sodium form B. U.S. Pat. No. 6,207,188 also provides a process for the preparation of such unstable omeprazole sodium form A. The disadvantage of the described process is that it is time consuming since it takes more than 3 days to be completed.

U.S. Patent Application Publication US 2004/0224987 A1 discloses a similar, although improved, process for the preparation of omeprazole sodium form A, which comprises the steps of dissolving omeprazole in an aqueous base, $Na^+ B^-$, wherein $Na^+$ donates sodium and B donates hydroxide or alkoxide, ion exchangers, resins which release sodium cation at room temperature in an appropriate solvent consisting of $C_3$-$C_7$ branched or chained hydrocarbons, $C_2$-$C_7$ branched or chained ethers, cyclic ethers, lower fatty acid esters, aliphatic ketone solvents, halogenated hydrocarbon solvents or nitrile solvents with optionally containing water, followed by neutralisation of resultant solution by an appropriate anti-solvent in which product is poorly soluble, stirring the reaction mixture for 0-24 hrs at room temperature, cooling the reaction mixture until the solid mass crystallises, filtering the isolated solid by conventional techniques, accompanied by washing with a solvent as mentioned above, drying the isolated compound at 30° to 70° C., preferably at a temperature of 50° to 60° C. to afford form A of omeprazole sodium. The resulting omeprazole sodium form A is stated to be more thermodynamically stable, non-hygroscopic and with permissible residual solvent limits. US 2004/0224987 further provides novel crystalline omeprazole sodium form C and crystalline omeprazole sodium form D and processes for preparation thereof.

In ES 2023778 a process for production of omeprazole metal salts, such as the sodium salt, using alkaline salt of active methylene compounds is disclosed.

Omeprazole salts in amorphous form and a process for the preparation thereof using spray-drying technique are disclosed in WO 01/87831.

The invention described in U.S. Pat. No. 6,262,085 provides 6-methoxy-2-[[(4-methoxy-3,5-dimethyl-2-pyridinyl) methyl]sulfinyl]-1H-benzimidazole or pharmaceutically acceptable salts thereof with explanation that making of a salt in solution results in the making of both compounds, having the methoxy group on the benzimidazole ring at the 6- and 5-position, due to tautomerization occurring in the solution.

Acetone complexes of sulfoxide compounds or pharmaceutically acceptable salts thereof of formula (I) are disclosed in patent EP-B-1 000 943, giving the examples for rabeprazole.

DESCRIPTION OF THE INVENTION INCLUDING EXAMPLES

Figure 1:
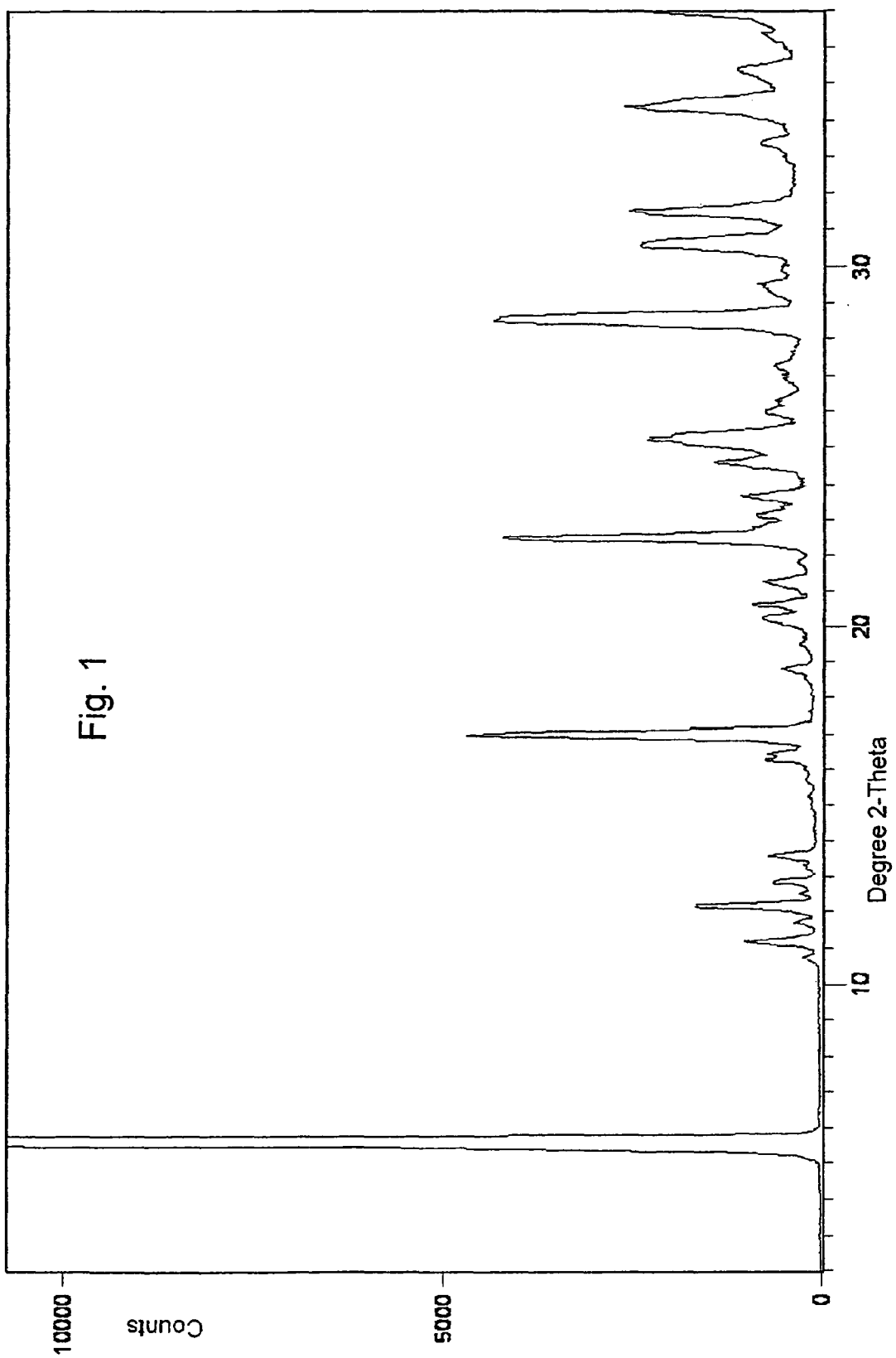
FIG. 1 shows a powder X-ray diffraction pattern of omeprazole sodium ethanol solvate.

An object of the present invention is to find a novel process for preparing omeprazole sodium form A with a low amount of residual solvents, which would be stable at ambient temperature. Further, the object of the present invention is directed to a novel crystalline omeprazole sodium form E and the related process of its preparation and to a novel crystalline omeprazole sodium form F and the related process of its preparation.

This problem has been solved by the present invention which relates to a novel stable crystalline omeprazole sodium ethanol solvate which is an intermediary compound in the novel process for the preparation of stable crystalline omeprazole sodium form A and in processes for the preparation of novel crystalline omeprazole sodium form E and a novel crystalline omeprazole sodium form F as well. X-ray powder diffraction (XRPD) is used as a method of differentiating between stable crystalline omeprazole sodium form A, novel stable crystalline intermediate omeprazole sodium ethanol solvate, novel stable crystalline omeprazole sodium form E and novel stable crystalline omeprazole sodium form F.

According to the present invention omeprazole sodium ethanol solvate is prepared by dissolving omeprazole (base) in a solution of NaOH in absolute ethanol. Mechanical particles are removed from the resulting solution, e.g. by filtration, and further seeded with crystals of omeprazole sodium form A to induce crystallisation. The slurry is then agitated for several hours at ambient temperature and additionally for several hours at low temperatures, e.g. from 0° to 5° C., in order to improve the yield. The precipitated omeprazole sodium form A is separated, e.g. by filtration or centrifugation, and washed with cooled absolute ethanol. Omeprazole sodium ethanol wet thus derived is dried under reduced pressure from 40° to 50° C., preferably at about 45° C. to yield stable anhydrous omeprazole sodium in ethanol solvate form. By the term "omeprazole sodium ethanol wet" is meant the product obtained before the step of drying under reduced pressure. The term "reduced pressure" generally refers to a pressure of about 10 mbar to about 50 mbar.

Omeprazole sodium ethanol solvate prepared by the process under anhydrous conditions according to the present invention contains from about 8 to about 11% by weight (as determined by gas chromatography) of residual ethanol incorporated in the crystalline lattice. This incorporated ethanol defines ethanol solvate crystalline form of omeprazole sodium and cannot be removed upon further drying. The water assay in omeprazole sodium ethanol solvate determined by thermogravimetric analysis or by Karl Fischer, techniques known per se, was found to be less than 0.5% by weight, which corresponds to anhydrous product.

Omeprazole sodium form A is highly soluble in water and as such, is suitable for parenteral formulations, providing an opportunity for physicians to treat patients suffering from gastroesophageal reflux disease (GERD) who are unable to take oral therapy. In this way, parenteral formulations of novel omeprazole sodium ethanol solvate with residual solvent incorporated in the solid would be pharmaceutically unacceptable, but is useful as a valuable intermediate for the preparation of crystalline forms of omeprazole sodium, substantially free of incorporated solvents. The term "substantially free" means less than 0.5% by weight of residual solvent, i.e. ethanol.

Thus, in order to obtain a hydrate of omeprazole sodium in the specific crystalline form, namely known form A, it is necessary to exchange ethanol that is incorporated in the crystalline lattice of omeprazole sodium ethanol solvate with molecules of water. We have surprisingly and unexpectedly found that the exchange may be conveniently performed by digesting novel omeprazole sodium ethanol solvate in a mixture of non-solvent and water. The term "digesting" is understood as a method in which a product is suspended in a solvent in which it is insoluble or poorly soluble, herein referred to as non-solvent, then a small amount of water is added and the resulting suspension is stirred for a defined period of time.

More specifically, omeprazole sodium ethanol solvate is converted to omeprazole sodium form A by the process of digesting the crystals of omeprazole sodium ethanol solvate in a mixture of suitable non-solvent and water. By the term suitable solvent is meant a non-solvent selected from the group consisting of diisopropyl ether, tert-butyl methyl ether, diethyl ether, ethyl acetate and acetonitrile, preferably diisopropyl ether, at the temperature range from 0° to 20° C., preferably from 50 to 10° C., for a period of 30 minutes to 10 hours, more preferably for about 4 hours. After completing the reaction the precipitated omeprazole sodium form A is then recovered, e.g. by filtration or centrifugation, in excellent yield and dried under conditions which avoid degradation of the desired product, e.g. at 40° to 50° C. under reduced pressure for 10 to 24 hours.

In another aspect of the present invention, instead of omeprazole sodium ethanol solvate, omeprazole sodium ethanol wet also may be used in the variant process of digesting but under the condition that it is previously washed with a suitable amount of non-solvent, selected from the group consisting of diisopropyl ether, tert-butyl methyl ether, diethyl ether, ethyl acetate and acetonitrile, preferably diisopropyl ether, before digesting it in a mixture of non-solvent and water. By the term "suitable amount of non-solvent" is meant the amount that will wash the residual ethanol from about 20% by weight to about 10% by weight, thus obtaining omeprazole sodium ethanol solvate. The whole process for the preparation of crystalline sodium form A starting from omeprazole (base) and using the washing of omeprazole sodium ethanol wet becomes thus less time consuming by avoiding the drying before the step of digesting.

Since omeprazole sodium in the crystalline form A is a hydrate with one to two moles of water per one mole of omeprazole sodium, at least about 10% to about 20% of water by weight regarding omeprazole sodium, preferably about 10% of water by weight, is needed in the process of digesting to obtain stable omeprazole sodium crystalline form A with a low amount of residual solvent.

The volume ratio in the mixture non-solvent:water used in the digesting process according to the present invention is in the range from 40:1 to 100:1, more preferably in the range from 60:1 to 80:1.

The level of residual solvents present in omeprazole sodium form A prepared by the process according to the present invention determined by gas chromatography, a technique known per se, was found to be below 0.5% by weight limit.

The water assay in crystalline omeprazole sodium form A prepared by the process according to the present invention determined by thermogravimetric analysis or by Karl Fischer, techniques known per se, was found to be from 6 to 8% what corresponds to one mol of water being bound in the crystal, i.e. 4.7%, while the other molecules of water are only absorbed on the crystal.

The present invention thus describes the process for the preparation of omeprazole sodium form A which comprises dissolving omeprazole (base) in solution of NaOH in absolute ethanol, inducing the crystallisation by seeding with crystals of omeprazole form A, isolation of the novel intermediate, i.e. anhydrous omeprazole sodium ethanol solvate, which is further converted into hydrate of omeprazole sodium, in the crystalline form A, by the process of digesting in the mixture of non-solvent and water. Accordingly, the present invention for the preparation of omeprazole sodium form A uses the conditions which are convenient to perform on an industrial scale and operationally safe. Another advantage of the process is that it is simple, economic and fast.

Additionally, we have found that omeprazole sodium form A prepared by the process according to the present invention is stable, substantially free of any other forms of omeprazole sodium, i.e. without detectable amounts of any other forms of omeprazole sodium, easy to handle and may be stored over an appreciable period of time without exhibiting a significant change physicochemical characteristics, e.g. chemical composition, hygroscopicity, solubility and crystalline form.

The stability of omeprazole sodium form A obtained by the processes of the present invention may be determined by standard protocol for characterisation of stability of a pharmaceutically active substance (EU: Adopted by CPMP, March 2003, issued as CPMP/ICH/2736/99—"Committee for proprietary medical products; Note for Guidance on ICH Q1A (R2) Stability testing guidelines: Stability testing of new drug substances and products"). Packed omeprazole sodium form A was aged for a definite period of time (1 month, 3 months, 6 months) under accelerated conditions of aging (at a temperature of 40° C. and 75% relative humidity which is a standard accelerated condition for stability testing of pharmaceutical formulations) and/or stress condition of aging (at a temperature of 60° C. which is a standard stress condition for stability testing of pharmaceutically active substances). Determination of absorbance measured according to the PhEur method (PhEur 3 Suppl 2000) was used as a criterion for evaluation of the sample quality during stability testing. It has previously been shown that measurement of absorbance is a more sensitive method for monitoring the process of omeprazole sodium decomposition than, for example, detection of present impurities using chromatographic methods (PhEur 3 Suppl 2000).

Figure 2:
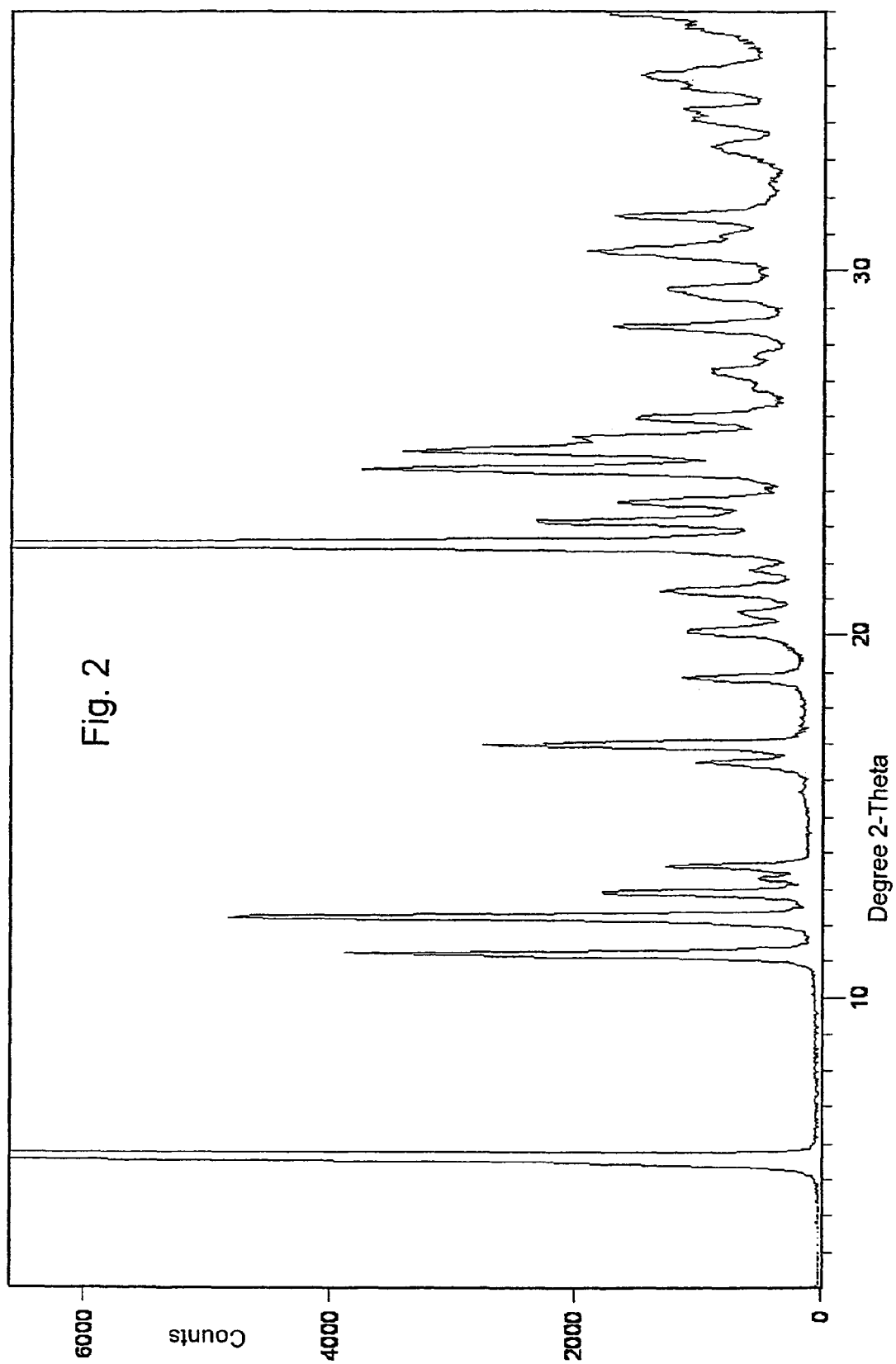
FIG. 2 shows a powder X-ray diffraction pattern of omeprazole sodium form A prepared by the process according to the present invention.

Omeprazole sodium ethanol solvate and omeprazole sodium form A, prepared according to the simple and improved process of the present invention, were analysed using X-ray powder diffraction (XRPD) pattern and gave the diffractograms depicted in FIG. 1 and FIG. 2. The main peaks, with positions and relative intensities, have been extracted from the diffractograms and given below in Table 1. The positions of the peaks (d values) in both cases were determined according to the standard procedure (Kug, H. P. & Aleksander, L. E., 1974). The relative intensities are less reliable and instead of numerical values the following definitions are used:

| Relative Intensity | Definition |
| --- | --- |
| 25-100 | very strong |
| 10-25 | strong |
| 3-10 | medium |
| 1-3 | weak |
| <1 | very weak |

Some additional peaks with low intensities found in the diffractograms have been omitted from Table 1.

Figure 5:
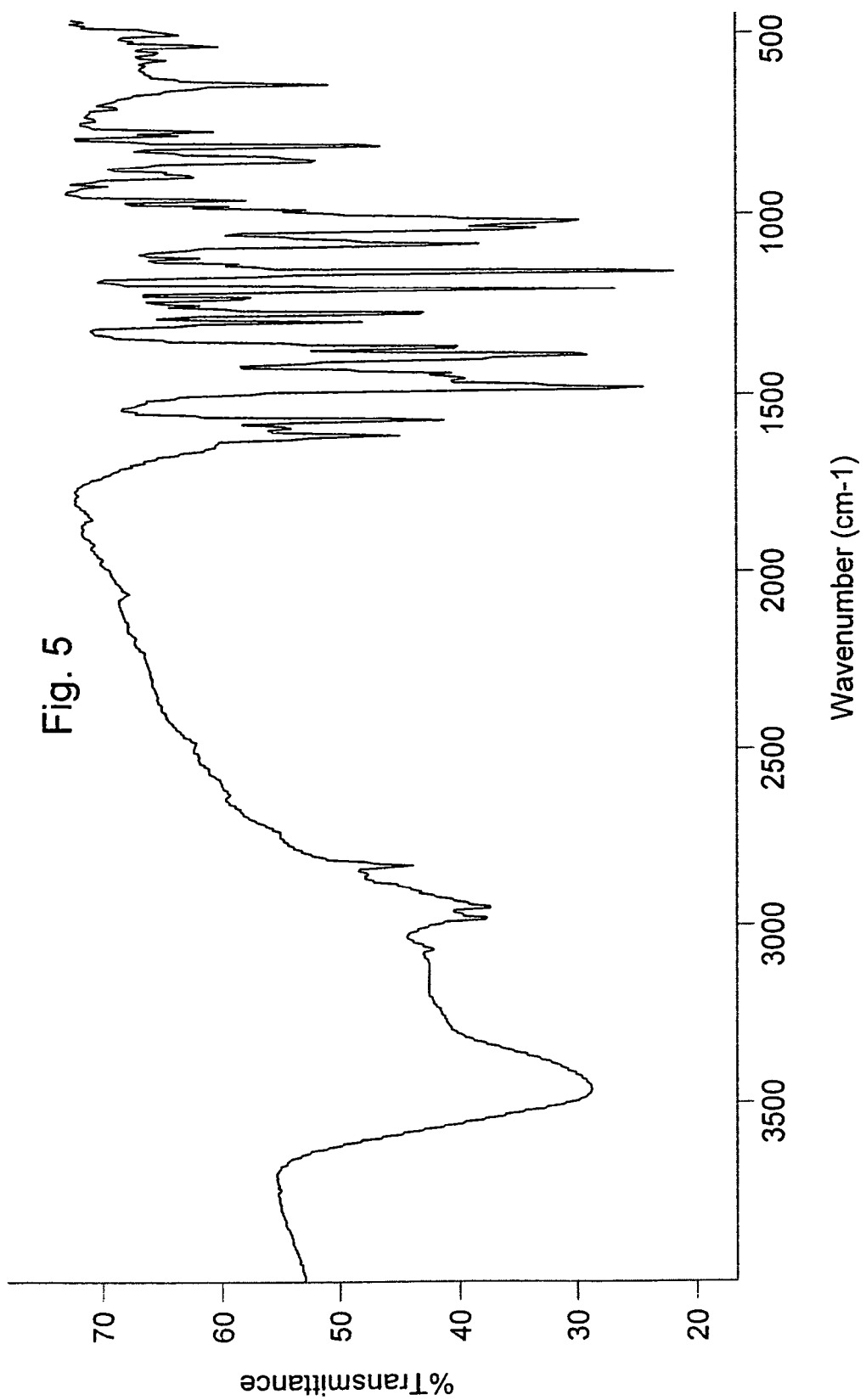
FIG. 5 shows an IR spectrum of omeprazole sodium ethanol solvate.
Figure 9:
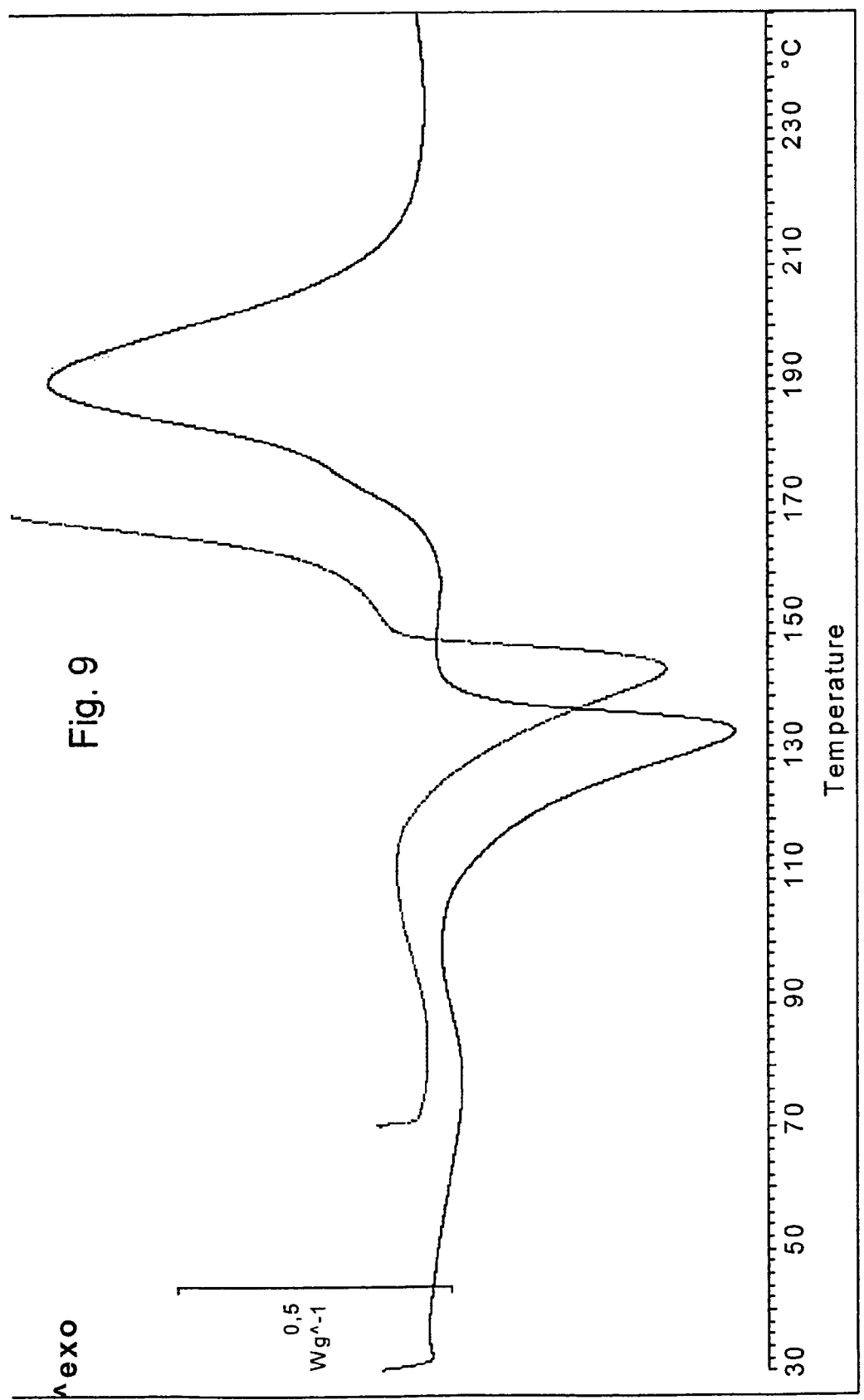
FIG. 9 shows a differential scanning calorimetry curve (DSC) of omeprazole sodium ethanol solvate (solid line) and omeprazole sodium form A (dotted line) as prepared according to the present invention.

Additionally, novel omeprazole sodium ethanol solvate of the present invention has the IR spectrum of FIG. 5 and the differential scanning calorimetry curve (DSC) of FIG. 9 (solid line).

Figure 6:
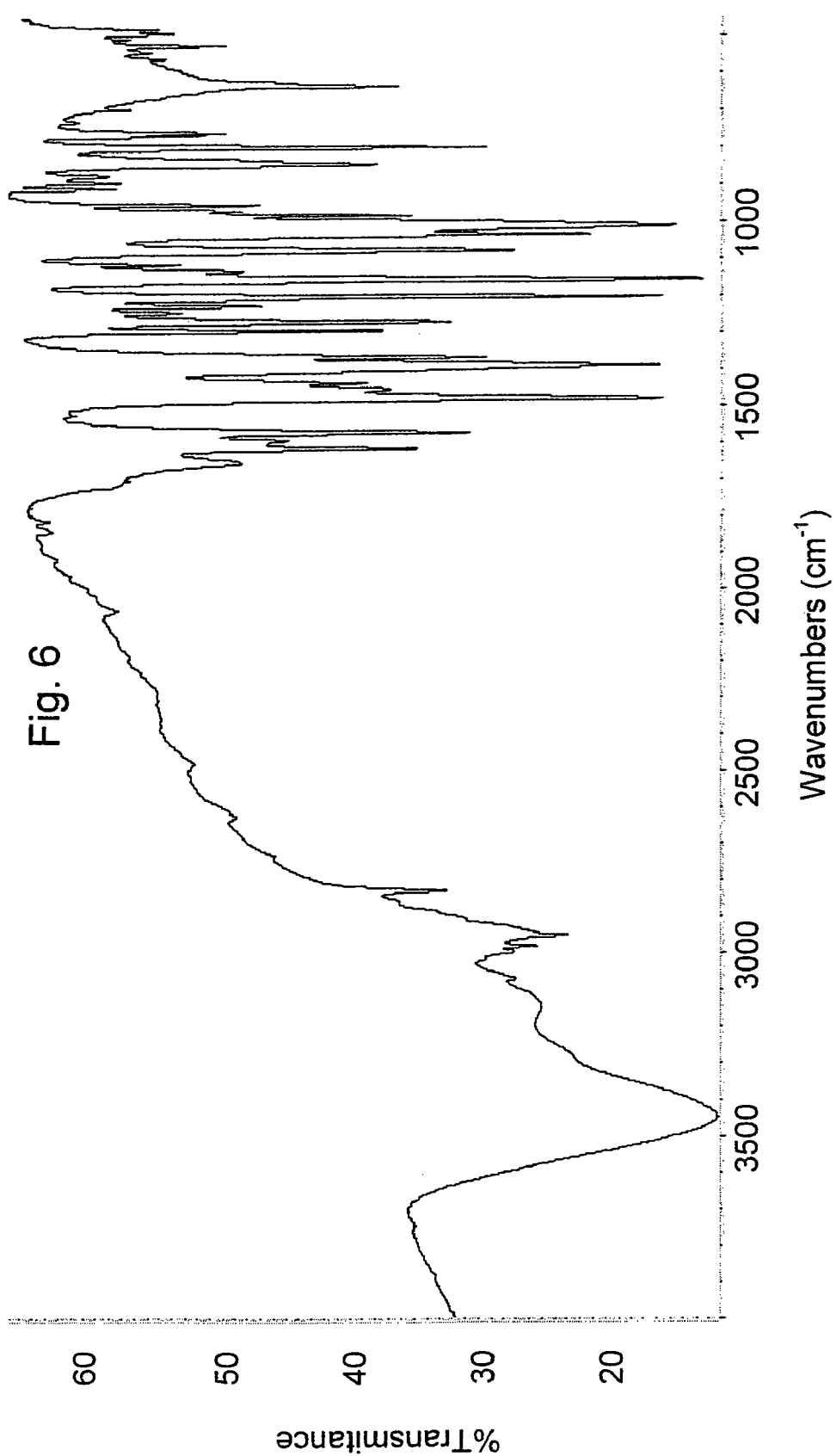
FIG. 6 shows an IR spectrum of omeprazole sodium form A prepared by the process according to the present invention.

Crystalline omeprazole sodium form A prepared according to the present invention has the IR spectrum of FIG. 6 and the differential scanning calorimetry curve (DSC) of FIG. 9 (dotted line).

TABLE 1

Positions and intensities of the major peaks in the XRPD of omeprazole sodium ethanol solvate and omeprazole sodium form A prepared according to the present invention

| omeprazole sodium ethanol solvate | | omeprazole sodium form A | |
| --- | --- | --- | --- |
| d value/Å | relative intensity | d value/Å | relative intensity |
| 15,659 | very strong | 15,651 | very strong |
| 8,246 | weak | | |
| 7,910 | weak | 7,913 | strong |
| 7,554 | weak | | |
| 7,262 | weak | 7,251 | very strong |
| 6,876 | weak | 6,861 | medium |
| 6,663 | weak | 6,660 | medium |
| 6,515 | weak | 6,491 | medium |
| 5,441 | weak | | |
| 5,383 | weak | 5,376 | medium |
| 5,221 | medium | 5,222 | strong |
| 4,717 | weak | 4,710 | medium |
| 4,552 | weak | | |
| 4,390 | weak | 4,416 | medium |
| 4,307 | weak | 4,308 | medium |
| 4,180 | weak | 4,185 | medium |
| 4,073 | weak | 4,074 | medium |
| 3,948 | medium | 3,945 | very strong |
| 3,844 | weak | 3,839 | strong |
| 3,759 | weak | 3,754 | medium |
| 3,620 | weak | 3,621 | strong |
| 3,527 | medium | 3,551 | strong |
| | | 3,499 | strong |
| 3,426 | weak | 3,428 | medium |
| 3,385 | weak | | |
| 3,311 | weak | 3,323 | medium |

TABLE 1-continued

Positions and intensities of the major peaks in the XRPD of omeprazole sodium ethanol solvate and omeprazole sodium form A prepared according to the present invention

| omeprazole sodium ethanol solvate | | omeprazole sodium form A | |
|---|---|---|---|
| d value/Å | relative intensity | d value/Å | relative intensity |
| 3,270 | weak | 3,269 | medium |
|  |  | 3,220 | medium |
| 3,126 | medium | 3,130 | medium |
| 3,043 | weak | 3,046 | medium |
| 3,027 | weak | 3,027 | medium |
| 2,918 | medium | 2,926 | strong |
|  |  | 2,886 | medium |
| 2,839 | medium | 2,841 | medium |

On the basis of the presented analytical data, it seems that omeprazole sodium ethanol solvate and omeprazole sodium form A represent similar compounds but close examination of both diffractograms shows there are peaks in one diffractogram that are not present in the other and vice versa, and also differences in intensities among peaks are huge which is not due to preferential orientation. Obviously, omeprazole sodium ethanol solvate and omeprazole sodium form A, as one being solvate and the other hydrate, crystallize in different crystal structures thus having different physicochemical properties, including melting point, solubility, hygroscopicity, and stability.

In another aspect of the present invention we have surprisingly and unexpectedly found two novel crystalline polymorphic forms of omeprazole sodium, namely omeprazole sodium form E and omeprazole sodium form F, which are disclosed herein.

Simple processes for conversion of omeprazole sodium ethanol solvate into omeprazole sodium form E and omeprazole sodium form F which are substantially free from any other forms of sodium salts of omeprazole, such as omeprazole sodium form A and with considerably low levels of residual solvents are also disclosed herein.

The above term "any other form" refers to anhydrates, hydrates, solvates and amorphous material, including polymorphs disclosed in the prior art.

Figure 3:
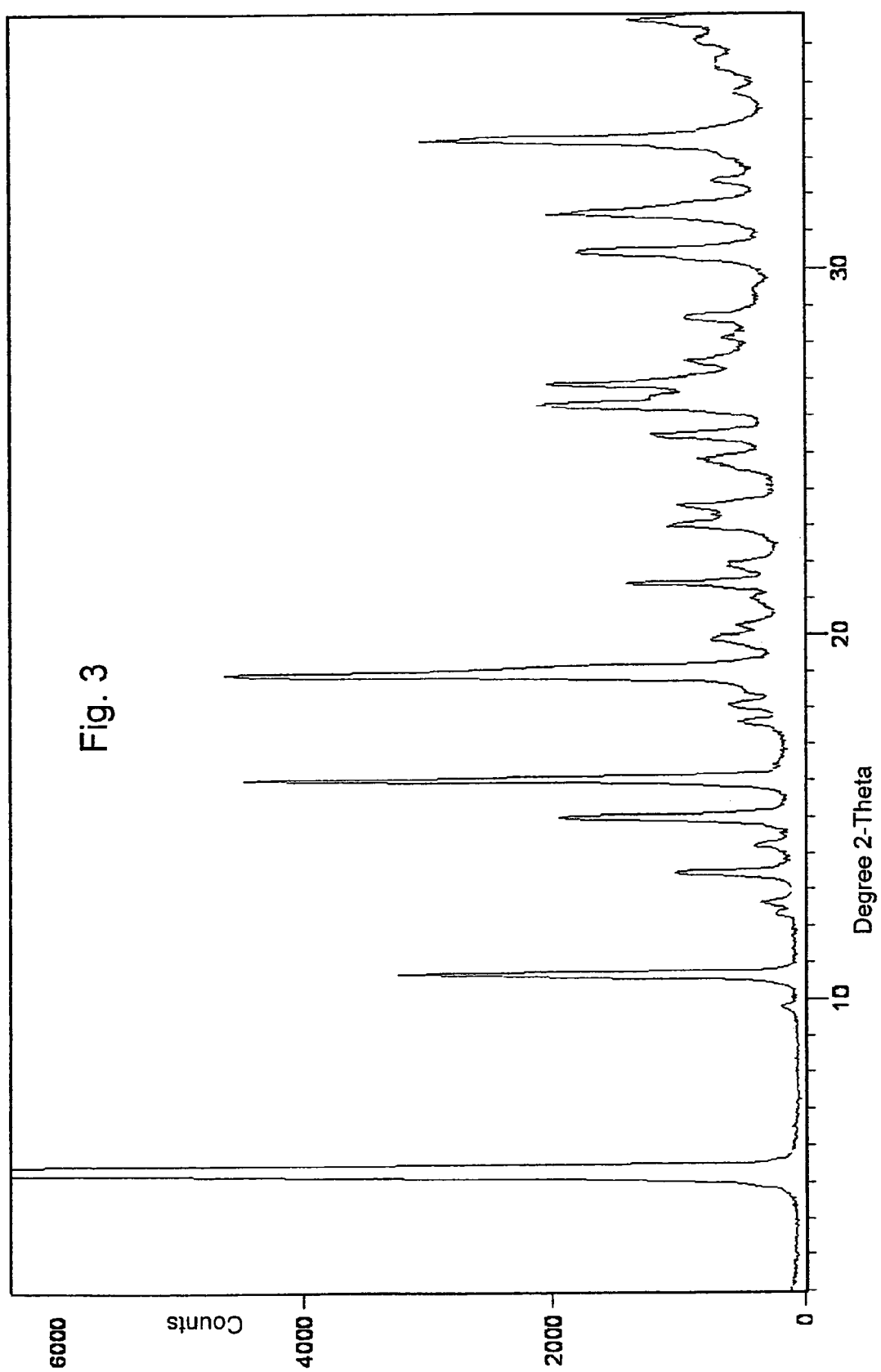
FIG. 3 shows a powder X-ray diffraction pattern of omeprazole sodium form E.
Figure 4:
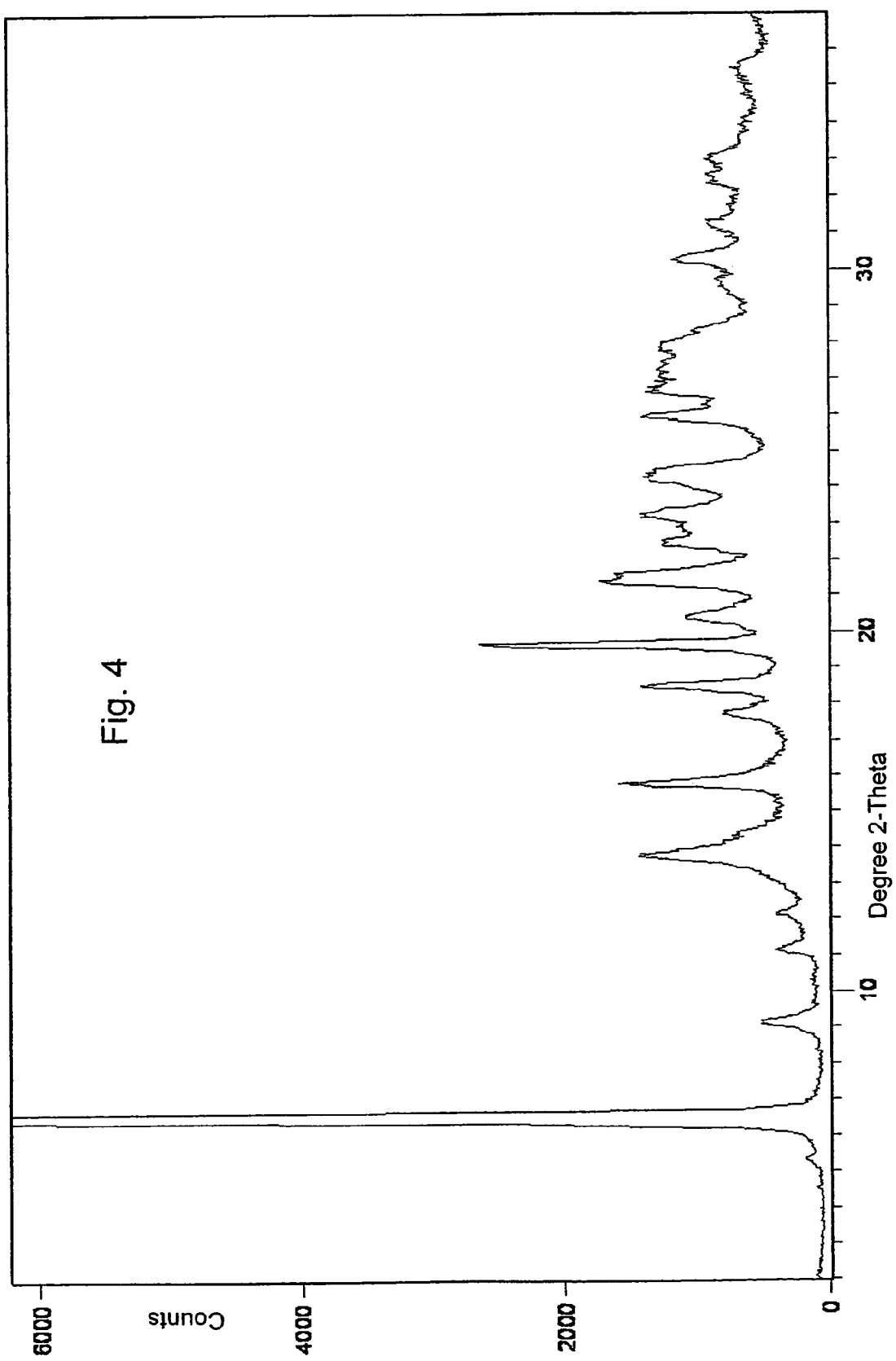
FIG. 4 shows a powder X-ray diffraction pattern of omeprazole sodium form F.
Figure 8:
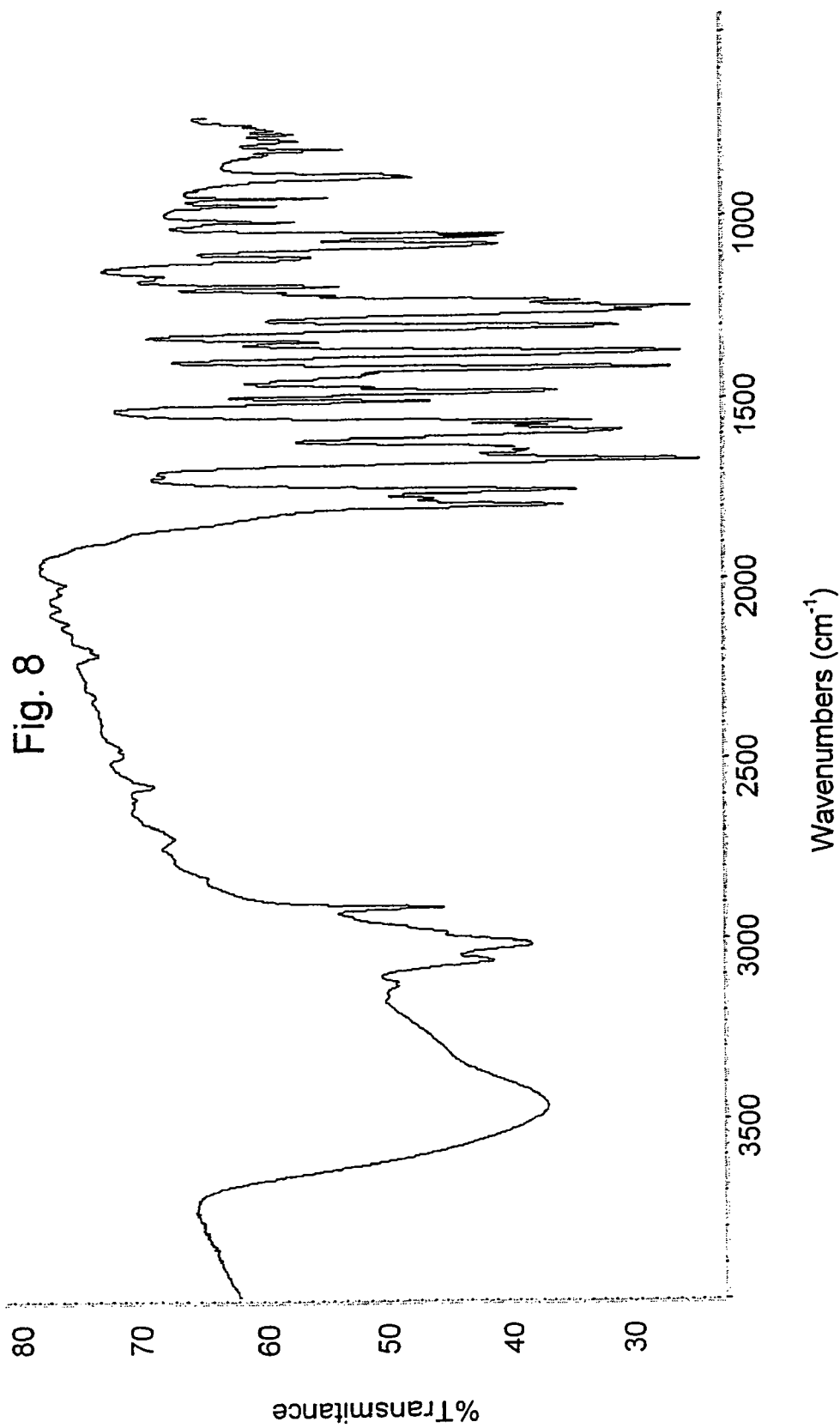
FIG. 8 shows an IR spectrum of omeprazole sodium form F.

The two novel crystalline forms, omeprazole sodium form E and omeprazole sodium form F, are characterized by their X-ray powder diffraction (XRPD) patterns as shown in FIG. 3 and FIG. 4 and by IR spectra as shown in FIG. 8 and FIG. 9, respectively. These characteristics are not exhibited by any other form of omeprazole sodium known in the prior art.

Omeprazole sodium form E is characterised by very strong X-ray diffraction peak at about 5.33±0.2 degrees 2-theta. It is further characterized by peaks of strong relative intensities at about 10.66, 16.02, 19.01, 26.29 and 33.47±0.2 degrees 2-theta; and with peaks of medium relative intensities at about 13.48, 14.98, 19.89, 21.42. 23.02, 25.47, 30.43 and 31.47±0.2 degrees 2-theta.

Omeprazole sodium form F is characterized by very strong X-ray diffraction peak at about 6.52±0.2 degrees 2-theta. It may further be characterized by a peak of strong relative intensity at about 19.63±0.2 degrees 2-theta; and with peaks of medium relative intensities at about 13.79, 15.76, 18.47, 20.38, 21.50, 22.50, 23.22, 24.28 and 25.96±0.2 degrees 2-theta.

A further objective of the present invention relates to simple processes for the preparation of two novel crystalline forms omeprazole sodium form E and omeprazole sodium form F, respectively.

We have unexpectedly found that by recrystallisation of omeprazole sodium ethanol solvate from a suitable solvent, selected from the group consisting of acetone, ethyl methyl ketone, 4-methyl-2-pentanone or cyclohexanone, a novel omeprazole crystalline form of omeprazole sodium with a low content of residual solvents may result.

Thus, omeprazole sodium ethanol wet or dried omeprazole sodium ethanol solvate as intermediary compounds prepared as described above (see also example 1 and example 2) may be converted into novel omeprazole sodium form E or novel omeprazole sodium form F by recrystallization from the above described selected solvents, preferably at room temperature. Which one of the two novel crystalline forms of omeprazole sodium may be obtained depends on the selection of the above described solvent used in recrystallisation of the intermediate. Precipitated crystals of novel omeprazole sodium forms are collected, e.g. by filtration, and dried under reduced pressure at about 45° C.

Thus, recrystallisation of omeprazole sodium ethanol solvate from acetone or cyclohexanone gives omeprazole form E, an anhydrous product, with an amount of organic solvent lower than 0.1% by weight.

Recrystallisation of omeprazole sodium ethanol solvate from 4-methyl-2-pentanone yields omeprazole sodium form F, an anhydrous material, with a little bit higher level of residual solvent, i.e. about 1% by weight.

Recrystallisation of omeprazole sodium ethanol solvate from ethyl methyl ketone gives a mixture of both forms, namely omeprazole sodium form E and omeprazole sodium form F, an anhydrous material, with an amount of residual solvents around 0.3% by weight.

Residual solvents in omeprazole sodium form E and omeprazole sodium form F may be determined by gas chromatography.

The water assay in omeprazole sodium form E and omeprazole sodium form F may be determined by thermogravimetric analysis or by Karl Fischer, techniques known per se.

Omeprazole sodium form E and omeprazole sodium form F are easy to characterize because they exist in a well-defined crystalline state. Both said novel forms of omeprazole sodium may be prepared in a simple and reproducible manner.

Omeprazole sodium form E and omeprazole sodium form F are stable compounds under special conditions (stored under nitrogen atmosphere) since both are hygroscopic and they will absorb up to about 7% by weight of water from air, depending on the relative humidity of the air. Both said novel forms of omeprazole sodium may be adversely converted to known crystalline omeprazole sodium form A by such absorption of water from air.

EP-B-1 000 943 describes also a process for preparation of acetone complex of sodium salt of sulfoxide compounds (e.g. rabeprazole sodium) by recrystallisation in acetone or in a mixture of acetone with solvent, e.g. n-hexane, isopropyl ether, toluene and ethyl acetate.

According to NMR studies as well as GC (gas chromatography) analysis performed we have proved that no complex was formed in the process of recrystallisation of omeprazole sodium ethanol solvate in acetone.

It is known that omeprazole is a useful proton pump inhibitor and can be used for the control of gastric acid secretion in mammals and especially in man. In particular, omeprazole sodium form A, as well as novel omeprazole sodium form E and omeprazole sodium form F, may be used for the prevention and treatment of gastric-acid related conditions, including for example, reflux esophagitis, gastritis, duodenal ulcer, non ulcer dyspepsia, upper gastrointestinal bleeding, stress ulceration, and gastronomas, in patients on NSAID therapy, and pre-operative and post-operative to prevent aspiration of gastric acid. Further, omeprazole sodium form A, as well as both novel omeprazole forms E and F, may be useful in the treatment of psoriasis and in the treatment of *Helicobacter* infections and related diseases.

The preparation of pharmaceutical compositions containing omeprazole sodium form A and/or form E and/or form F, substantially free of residual solvents and pharmaceutically acceptable excipients, is also disclosed herein. The pharmaceutical compositions are suitable for oral and parenteral administration. The most suitable route of administration as well as magnitude of a therapeutic dose of omeprazole sodium according to the invention in any given case will depend on the nature and severity of the disease to be treated. The dose and dose frequency may also vary according to the age, body weight, and response of the individual patient. In general, a suitable dose of the active ingredient is within the range of 10 mg to 80 mg daily, preferably between 20 to 40 mg of total daily dosage. Dosage forms include capsules, tablets, dispersions, solutions, suspensions, emulsions, gels, and powders.

Methods

X-Ray Powder Diffraction: Siemens d-5000 powder diffractometer using reflection geometry and CuKa radiation in the range from 2 to 37° 2θ in step of 0.03° 2θ, integration time was 5 second per step and the slits were set to 20 mm (variable divergence) and 0.6 mm (receiving).

FT-Infrared: Nicolet Nexus FTIR spectrophotometer using potassium bromide pellet method with 16 scans and 2 cm$^{-1}$ resolution, scanning from 400 to 4000 cm$^{-1}$.

Diffraction Scanning Calorimetry: Mettler Toledo DSC822$^e$ differential scanning calorimeter, the sample (4-8 g) was placed in an unsealed aluminium pan with one hole and heated at 3° K/min in the temperature range from 70° C. to 170° C. in the air atmosphere.

Gas Chromatography: column RTX 624, 30 m×0.53 mm; $T_{starting}$=40° C., $T_{gradient}$=40° C./min till 200° C., 5 min; injector: splitless, T=140° C.; detector: FID, T=200° C.; mobile phase: helium, 5 psi; $T_{oven}$=80° C.; sample: 115 mg/mL DMA (N,N-dimethyl acetamide).

The invention is illustrated by the following Examples:

Example 1

Preparation of Omeprazole Sodium Ethanol Wet from Omeprazole

Into solution of NaOH (36.5 g, 0.91 mol) in absolute ethanol (650 mL) omeprazole (300 g, 0.87 mol) is added. The slurry is stirred for 20 minutes at ambient temperature. The resulting solution is filtered through a layer of celite and charcoal on a Büchner funnel of porosity B4. The solution is seeded with omeprazole sodium form A (1 g) to initiate the crystallisation and stirred at ambient temperature for 8 hours. The formed slurry is stirred for an additional 8 h at the temperature range from 0° to 5° C. and the product is filtered off and washed with absolute ethanol (100 mL), cooled to 5° C. to yield 289 g of omeprazole sodium ethanol wet.

Example 2

Preparation of Omeprazole Sodium Ethanol Solvate 289 g of omeprazole sodium ethanol wet obtained as described in Example 1 was dried at reduced pressure at 45° C. overnight to yield 245 g of omeprazole sodium ethanol solvate.

Water content % (w/w by TgA)<0.5%.

Powder XRDP, IR (in KBr) and DSC are shown in FIGS. 1, 5 and 9 (solid line).

Example 3

Preparation of Omeprazole Sodium Form A 289 g of omeprazole sodium ethanol wet from Example 1 is additionally washed three times with 300 mL of diisopropyl ether and transfered into a 5 L reactor. Diisopropyl ether (3 L) and water (45 mL) were added and the slurry intensively stirred for 4 hours at 5° C. Crystals are separated by filtration and dried under reduced pressure at 45° C. overnight to yield 220 g of omeprazole sodium form A.

Water content % (w/w by TgA)=7.5%

Powder XRDP, IR (in KBr) and DSC are shown in FIGS. 2, 6 and 9 (dotted line).

Example 4

Preparation of Omeprazole Sodium Form E 15 g of dried omeprazole sodium ethanol solvate from Example 2 is dissolved in acetone (150 mL). After stirring the solution overnight at ambient temperature the resulting product is filtered off and dried under reduced pressure at 45° C. overnight to yield 11.5 g of the title product.

Water content % (w/w by TgA)<0.5%.

Figure 7:
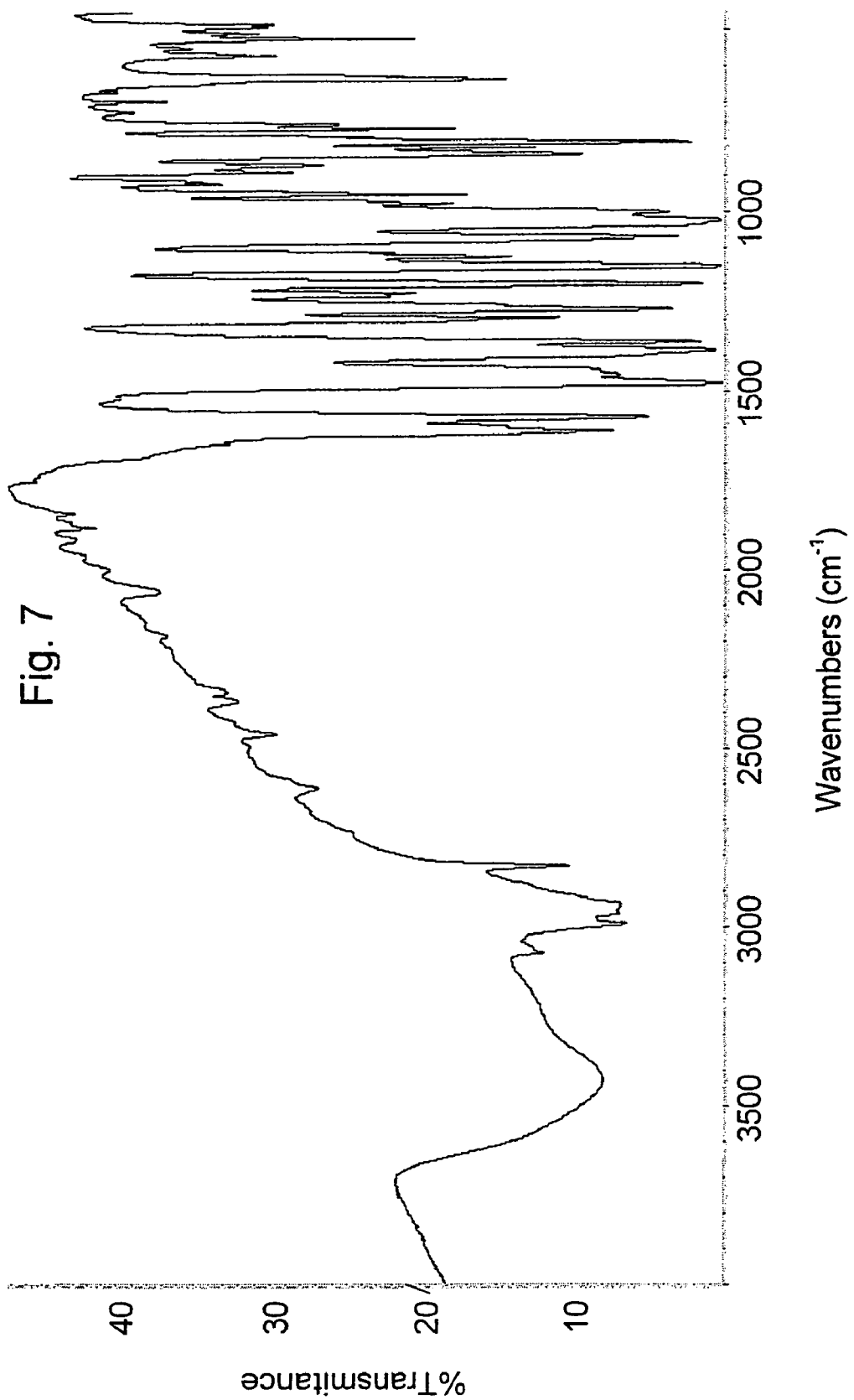
FIG. 7 shows an IR spectrum of omeprazole sodium form E.

Powder XRPD and IR (in KBr) are shown in FIGS. 3 and 7.

Example 5

Preparation of Omeprazole Sodium Form F 20 g of dried omeprazole sodium ethanol solvate from Example 2 is dissolved in 4-methyl-2-pentanone (400 mL). After stirring the solution overnight at ambient temperature the resulting product is filtered off and dried under reduced pressure at 45° C. overnight to yield 16.4 g of the title product.

Water content % (w/w by TgA)<0.5%.

Powder XRDP and IR (in KBr) are shown in FIGS. 4 and 8.

The invention claimed is:

1. A Crystalline omeprazole sodium ethanol solvate having an X-ray powder diffraction (XRPD) pattern containing peaks substantially as set out in Table 1.

2. The Crystalline omeprazole sodium ethanol solvate according to claim 1, wherein it provides an X-ray powder diffraction pattern substantially in accordance with FIG. 1.

3. The Crystalline omeprazole sodium ethanol solvate according to claim 1, wherein the content of ethanol in said compound amounts from 8% to 11% by weight.

4. The Crystalline omeprazole sodium ethanol solvate according to claim 1, wherein the content of water in said compound is less than 0.5% by weight.

* * * * *